United States Patent [19]

Silver

[11] 4,409,329

[45] Oct. 11, 1983

[54] SACCHARIFICATION METHOD

[75] Inventor: Richard S. Silver, Monroeville, Pa.

[73] Assignee: Gulf Research & Development Company, Pittsburgh, Pa.

[21] Appl. No.: 398,618

[22] Filed: Jul. 15, 1982

Related U.S. Application Data

[63] Continuation-in-part of Ser. No. 243,296, Mar. 24, 1981, abandoned.

[51] Int. Cl.[3] .......................... C12P 19/02; C12P 7/06

[52] U.S. Cl. .................................... 435/105; 435/161; 435/162; 435/163; 435/165

[58] Field of Search .................. 435/93, 99, 105, 161, 435/162, 163, 165, 305, 307, 813

[56] References Cited

U.S. PATENT DOCUMENTS 755,390 3/1904 Reynaud ........................ 435/161 X
3,308,037 3/1967 Goos et al. ........................... 435/99
3,337,414 8/1967 Wilson ............................. 435/99 X
3,679,431 7/1972 Clayton et al. .................. 435/93 X
3,990,944 11/1976 Gauss et al. ......................... 435/165
3,990,945 11/1976 Huff et al. ...................... 435/252 X
4,009,075 2/1977 Hoge .............................. 435/165 X
4,224,410 9/1980 Pemberton et al. ........... 435/165 X

FOREIGN PATENT DOCUMENTS 724567 3/1980 U.S.S.R. ............................. 435/161

*Primary Examiner*—Robert A. Yoncoskie
*Attorney, Agent, or Firm*—Deane E. Keith; Forrest D. Stine; Donald L. Rose

[57] ABSTRACT

Enzymic conversion of cellulose under mechanical shear rate of from 50,000 to 200,000 feet/minute/foot as imparted to the cellulose by a series of rotors and stators mounted in the reaction vessel improves yield of simple sugars.

10 Claims, 6 Drawing Figures

C-2.0
B-1.0
Shearing Power
Units/Liter
A-Zero
Cellulose Concentration
4 wt% all curves
Hydrolysis Reaction Rate
200
100
0
0
1
2
3
Enzyme Concentration, Units /ml 13
6
5
7
2
3
3
4
15
1
14
6
7
2
3
3
4
12

SACCHARIFICATION METHOD

This application is a continuation-in-part of U.S. Ser. No. 243,296, filed Mar. 24, 1981, now abandoned.

BACKGROUND OF THE INVENTION

Cellulose is one of the most abundant carbonaceous materials available on earth; some billion tons of cellulose are being formed annually by the natural process of photosynthesis. Efficient and economic conversion of cellulose to compounds such as ethanol which can serve as fuels and chemical feedstocks could significantly reduce our dependence on non-renewable, hydrocarbon-derived resources.

Gauss et al., U.S. Pat. No. 3,990,944, and others, have demonstrated that biological conversion of cellulose using microorganisms and/or enzymes to ethanol or other chemicals is a specific and expeditious method of utilizing this resource. However, no such biological process has yet reached large-scale commercial practice due to the uncertain economic feasibility of these operations. The invention described herein provides a substantial improvement over the prior art, which considerably reduces the cost of converting cellulose to ethanol or other chemicals.

In any biological process for cellulose conversion, a cellulose-containing feedstock such as wood processing wastes, sugarcane bagasse, pulping wastes, rice straw, or hydropulped municipal solid waste is contacted with a source of cellulolytic enzymes. The feedstock is generally pretreated by some physical, mechanical, chemical, thermal, or combination process to improve the access of the cellulolytic enzymes to the cellulose. This improvement occurs through particle size reduction and liberation of the cellulose from lignin and other feedstock components which hinder the access to enzyme. Previous investigations, e.g. those of Gum and Brown, Biochem. Biophy. Acta, 446, 370–386 (1976), have shown that the cellulase enzyme complex elaborated by the mold *Trichoderma reesei* QM 9414 contains a multiple of enzymes, e.g. an endoglucanase (E.C.3.2.1.4), and cellobiohydrolase (E.C.3.2.1.91) and a beta-glucosidase (E.C.3.2.1.21), needed for the rapid hydrolysis of cellulose to simple sugars such as cellobiose and eventually glucose. The formed and released soluble sugars can be fermented by yeasts such as *Saccharomyces cerevisiae* or *Candida brassicae* or bacteria such as *Zymomonas mobilis* or molds such as *Rhizopus javanicus* to ethanol.

It will be noted in the system described above there are four essential components:

1. A cellulose feedstock.
2. A source of cellulase enzyme complex.
3. Simple sugars such as glucose released by the action of cellulases on cellulose.
4. Microorganism capable of fermenting sugars to ethanol.

It is known by those skilled in that art that during the enzymatic hydrolysis of cellulose to sugars, the rate of the hydrolysis reaction can be restricted by several factors; for example, addition of a larger quantity or more potent enzyme to a given amount of cellulosic feedstock will generally increase the hydrolysis rate. However, as additional quantities of enzyme are added to the cellulose, less positive and then negative effects on the hydrolysis rate are observed, as shown in FIG. 1, curve A. This is most likely the result of the saturation of the active surface sites on the cellulose-containing particles by the surplus enzyme, whereupon addition of further enzyme has no beneficial effect. The rate of reaction is also limited by the concentration of cellulosic feedstock which can be suspended in the aqueous enzyme-containing reaction slurry. Above a certain concentration, the value of which depends on the specific feedstock, the viscosity of the liquid becomes so high that a plastic or semi-solid consistency is assumed, and pumping or mixing becomes difficult. It has been shown to be beneficial to add certain polymeric surface-active materials to the reactor during enzymatic hydrolysis to cellulose. Moo-Young, U.S. Pat. No. 3,975,236, discloses that materials such as high molecular weight carboxypolymethylenes can increase the production of cellulolytic enzymes during the growth of Trichoderma species on cellulose.

SUMMARY OF THE DISCLOSURE

It is the finding of the present invention that the rate of hydrolysis of cellulosic feedstock to simple sugars by cellulase enzyme complex can be substantially and unexpectedly increased if the reaction takes place in a reaction zone wherein an aqueous slurry comprising from 3 to 20 weight percent of a solid cellulose containing charge stock is contacted with a cellulase enzyme complex wherein the concentration of said enzyme complex is greater than 0.1 units per milliliter of said slurry in the presence of a mechanically produced shear rate of from 50,000 to 200,000 feet/minute/foot substantially throughout the reaction zone to continually expose fresh cellulose surface to the enzyme-containing slurry. It is to be noted that the stirrers or impellors found in conventional fermenters, whether baffled or unbaffled, do not provide the shearing action required by the present invention. The reaction of the present invention generally operates in the absence of air or oxygen, therefore, the shearing action is not of the type conventionally used to effect oxygen transfer. Further, the aqueous slurry of cellulase enzyme and cellulose containing feedstock is not the typical starch-water-enzyme gels which must be broken by lesser shear forces (U.S. Pat. No. 3,308,037).

DESCRIPTION OF THE DRAWINGS

The invention will be more readily apparent upon reading the following description in conjunction with the drawings in which.

DETAILED DESCRIPTION

The term "shear rate" as used in this invention is the differential in fluid velocity developed between two adjacent zones as limited by adjoining rotor and stator blades, divided by the distance between the zones. This differential in fluid velocity can be measured by the use of Pitot tubes or other known methods such as laser velocimeters (see "Fluid Mixing Variables in Suspension and Emulsion Polymerization", J. Y. Oldshue, et al., Chemical Engineering Progress, May, 1982, p. 68 et seq.). Thus, for example, if at the tip of the rotor the fluid velocity is 6000 ft/min, then the shear rate between the tip of the rotor and an adjacent point on the adjoining stator 0.1 ft away, is 60,000 feet/min/foot.

Figure 1:
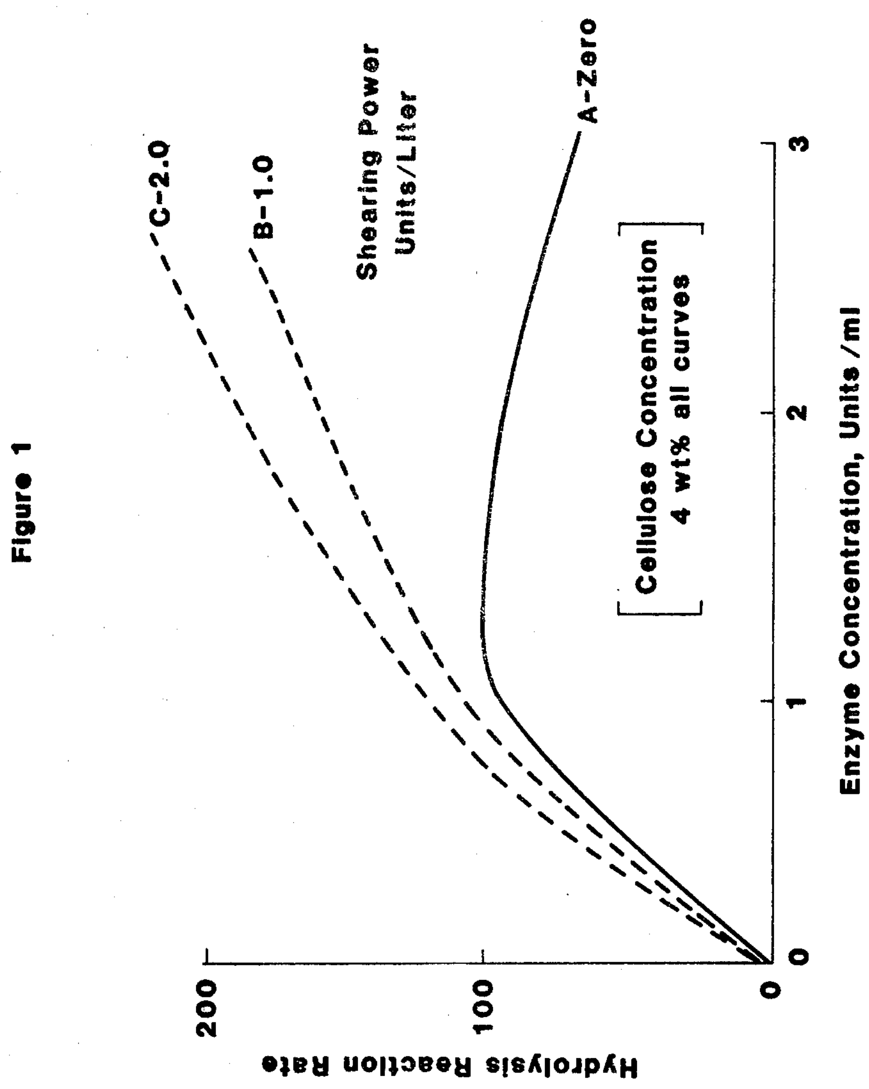
FIG. 1 is a graph showing the beneficial use of higher enzyme concentration with increased shear rate.

The shearing action disclosed in the present invention leads to the continual exposure of fresh cellulose surface, allowing the beneficial use of higher enzyme concentrations as shown in FIG. 1. It will be noted that in the absence of the specific shear (Curve A), increasing the enzyme concentration from 0.1 to 0.2 units has no effect on hydrolysis reaction rate, while in the presence of shear (Curve B, shear rate of 50,000 feet/minute/foot) the same enzyme concentration increases results in a rate increase of about 70%. Further increases in shear rate also have a beneficial effect (e.g. Curve C—shear rate of 200,000 feet/minute/foot) but diminishing returns in rate increase are realized as shear rate is further increased. Further, in addition to the above mentioned reaction rate increase, the shearing force also increases the ultimate conversion of cellulose to ethanol. Additional benefits are realized by the use of surface active agents and polymeric surfactants as poly-oxyalkalene-polyol-fatty acid ester, e.g. polyoxyethylene, sorbitan monooleate, which can increase the rate of non-growth hydrolysis of cellulose by cellulase enzymes in the presence of shearing forces and can also decrease the shearing power required to obtain a specific rate of hydrolysis.

The present invention can utilize many solid cellulosic feedstocks containing from 30 to 80 weight percent cellulose, including sugarcane bagasse, rice straw, corn stover, pulp mill wastes, hydropulped municipal waste, ground wood, etc.

The solid cellulosic charge stock is used in this invention as an aqueous slurry. The solid cellulose is preferably comminuted by any suitable technique to a small particle size. Usually, the mean particle size is from 0.01 to 1 inch in diameter, and the particular particle size is a function, normally, of the source of the cellulosic feedstock.

The aqueous slurry can contain from three to 20 weight percent of the solid cellulosic feedstock and preferably contains from 15 to 20 weight percent of such cellulosic materials. A higher concentration of cellulosic feedstock can be used without increasing liquid viscosity to the semi-plastic level. For example, in the absence of the shear rates of this invention, a suspension of approximately 10 wt.% of a cellulose-containing pulp mill waste is the maximum readily mixable. However, in the presence of the shear rates of the present invention, the aqueous slurry can contain from 15–20 wt.% of the cellulosic feedstock.

There are several devices which may be suitable for imparting the shear rates required in this invention, namely any devices which continually and in the simultaneous presence of enzyme-containing solution exposes fresh cellulose surface.

Figure 2:
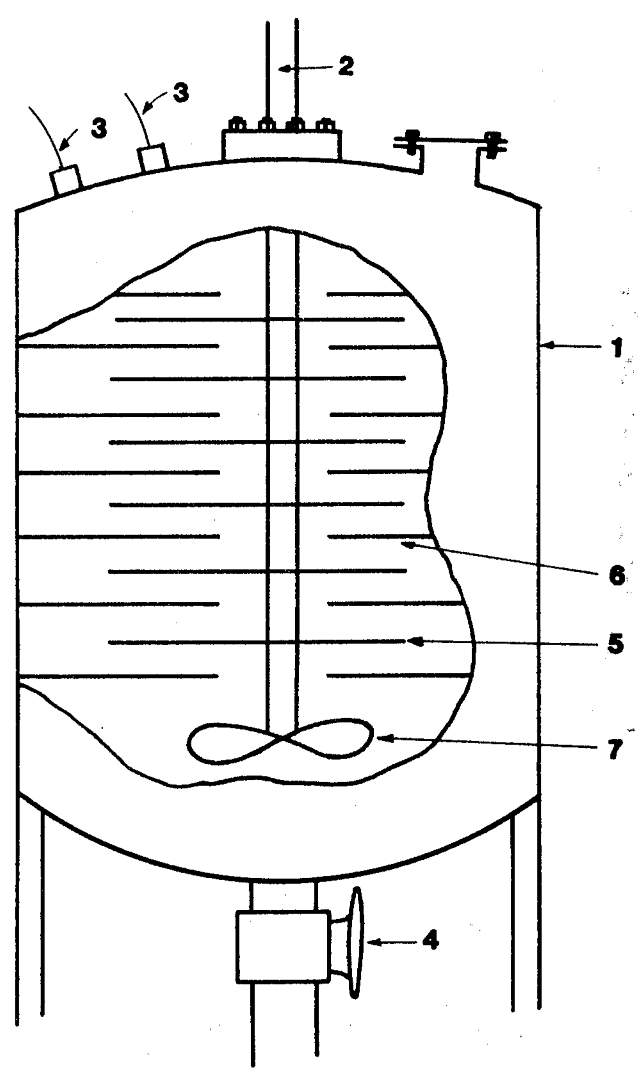
FIG. 2 is a diagram of a suitable vessel for carrying out the invention.
Figure 2A:
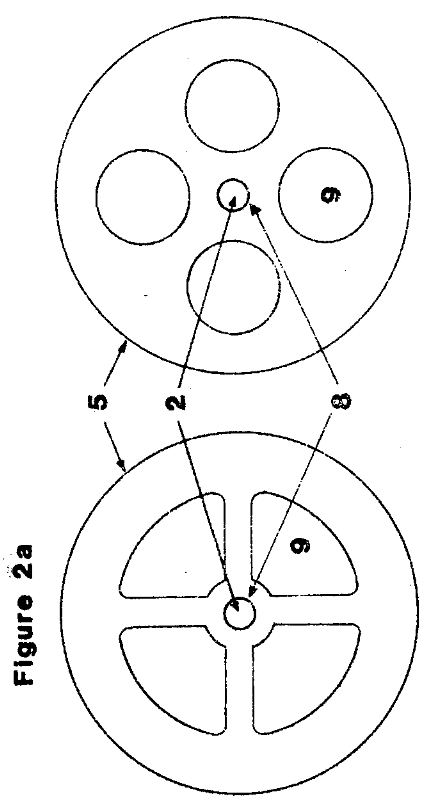
FIG. 2*a* is a diagram of perforated rotor blades for a device shown in FIG. 2.

A particular device which is effective is shown in FIG. 2. This comprises a cylindrical vessel 1 containing the usual sensing devices 3, wherein affixed to the walls are a number of non-moving, perforated stator blades 6. A concentric shaft 2 supports a number of perforated rotor blades 5 which alternate with the stator blades 6 and rotate between the two adjacent stators. The spacing between the rotor and stators varies with the feedstock employed, e.g. 0.1–50 mm, with the preferred spacing being 5–10 mm for a pulp mill waste. The blades may be constructed of thin sections of metal or other biologically inert material, and any individual blade may project over 0–100% of the cross-sectional area of the adjacent blade. Preferably an overlap of 30–70% of the adjacent blade is desired. The total volume occupied by blade material represents less than 50% and preferably less than 25% of the reactor internal volume. The blades are perforated to facilitate free vertical movement of the reactor slurry. The perforation voids which may be of varying shape, as for example circles or slots, comprise over 50% of the total blade area, FIG. *2a*.

If it is desired to promote vertical mixing, one or more propellers or similar devices 7 can be affixed to the rotor shaft. The speed of rotation of the rotor shaft can be varied to increase or decrease the power input and shear force on the cellulose particles.

The effective operation of the method of this invention requires at least some mechanical or other pretreatment of the cellulosic feedstock prior to introduction into the reactor such that substantially no particles are larger than the spacing between rotor an stator blades. However, a small amount of such larger particles will not preclude the operation.

Figure 3:
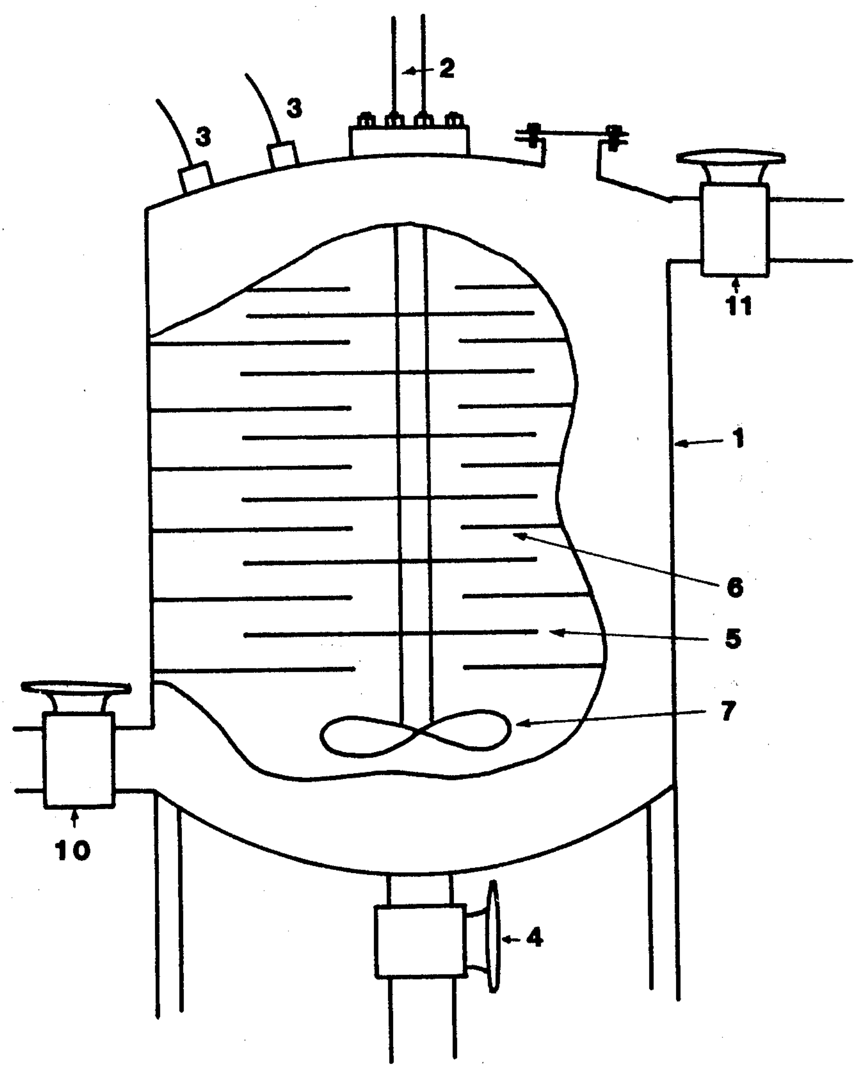
FIG. 3 is a diagram for a suitable vessel for continuous operation of the invention.

The reactor vessel 1 and the reaction system can be operated either in a batch or continuous mode. A continuous mode reactor operation is shown in FIG. 3. In a continuous operation the reactor is constantly fed through a valve 10 with a separately prepared enzyme-containing slurry and a cellulosic feedstock. Simultaneously, the reaction suspension is withdrawn from the reactor through valve 11 at a rate equal to feed volume so that reactor liquid volume is maintained constant by use of a control device 3. It is also possible to control the rate of continuous influx and efflux to and from the reactor by use of other mechanisms, e.g. via a device which monitors via light scattering from the turbidity of the reactor effluent, or a device which monitors the viscosity of the reactor contents. In this continuous mode, it is preferable to continuously and separately prepare the cellulase enzyme complex by the continuous propagation of a cellulase-producing microbe, e.g. *Trichoderma reesei* QM9414, in an aerobic culture vessel, and then to feed the entire, unseparated culture liquid to the reaction zone of this invention, following the teaching of Huff and Yata, U.S. Pat. No. 3,990,945. Such culture liquid is added to the reaction zone in sufficient quantity to provide a cellulase enzyme complex concentration within the range of 0.1 to 5 units per milliliter of total material within the reaction zone, i.e., the aqueous cellulosic containing slurry plus the cellulase enzyme complex. A cellulase enzyme complex unit is defined as that amount of cellulase enzyme complex which can release one micromole of glucose per minute from cellulose under standard reaction conditions as described in "Enzymic Activities of Endo-1,4-β-D-Glucanases Purified from Trichodera Viride", by S. P. Shoemaker and R. D. Brown, Jr., *Biochimica et Biophysica Acta,* Vol., 523, 1978 at p. 134.

Figure 4:
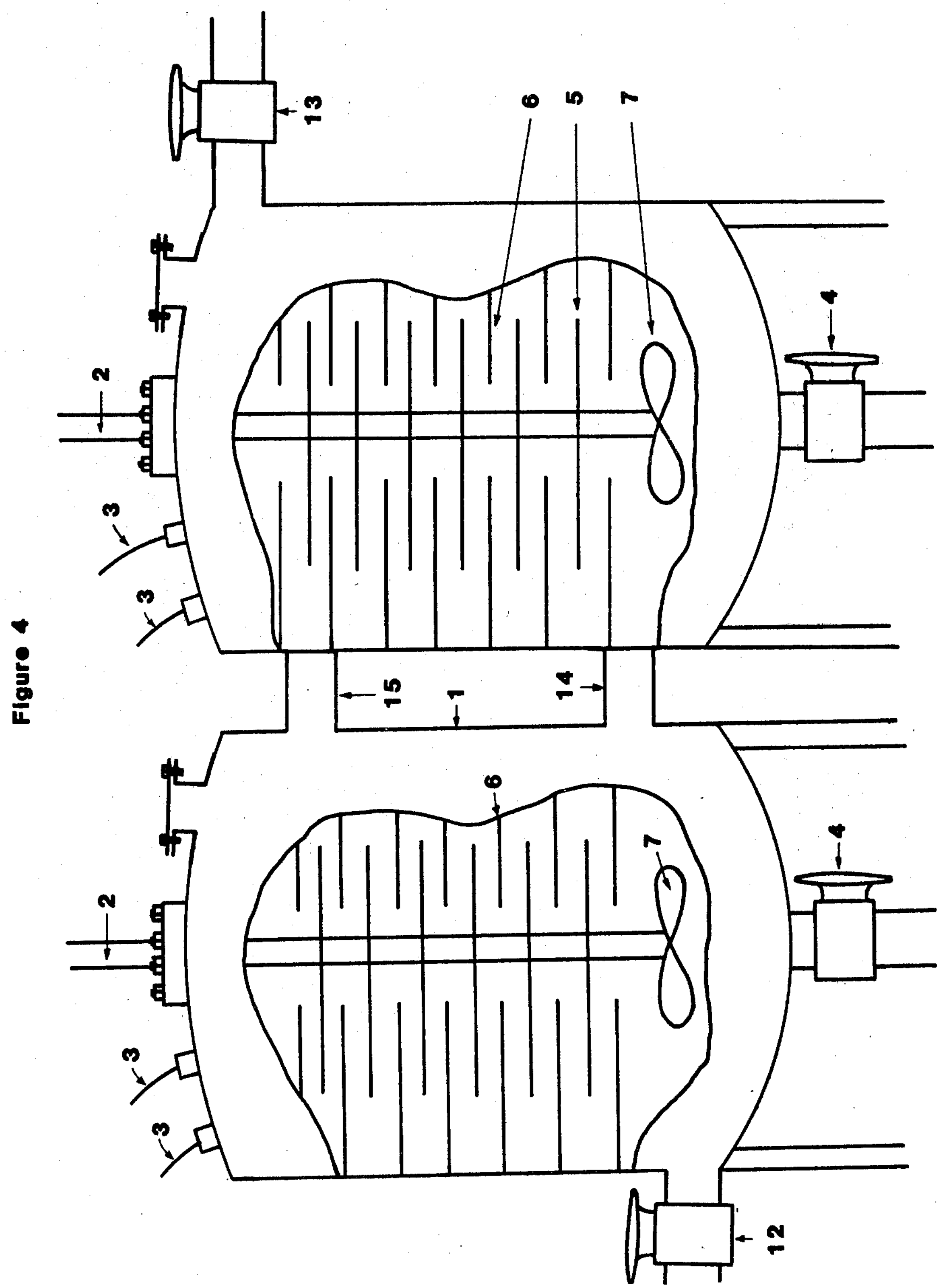
FIG. 4 is a diagram showning multiple vessels for continuous operation.

The continuous reactor of FIG. 3 may be operated either in a "plug flow" mode wherein material introduced into one end of the reactor travels through to the other end without significant axial backmixing, or alternatively in a "fully backmixed" mode wherein the reactor contents are essentially perfectly mixed, or in some intermediate mode with partial backmixing. If plug flow is desired, no propellers 7 are installed on the reactor shaft 2. The continuous reactor may consist of a single vessel or a number of essentially identical vessels connected in series wherein the effluent from the first constitutes the feedstock to the second and so on, FIG. 4.

It is a preferred embodiment of the present invention to simultaneously saccharify cellulose to glucose and other sugars and to ferment these sugars to ethanol in the same vessel wherein there is present a shearing force which continually exposes fresh cellulose surface. By this method, glucose and the simple sugars never accumulate to any significant extent, i.e., the concentration of produced sugar is at all times substantially zero in the reaction zone, and the enzymatic saccharification of the cellulose proceeds at a maximum rate. The shearing forces present in the reactor and specifically the blade spacing in a device of the type shown in FIG. 2, while of such magnitude to continually expose fresh cellulose surface on the particles of cellulosic feedstock and achieve the benefits described in this invention are not of such magnitude or frequency such as to damage or decrease the activity of either the fermentative microbe, e.g. *Candida brassicae*, or of the cellulase enzyme complex. Also, as Gauss et al. loc. cit, unexpectedly observed, *Trichoderma cellulase* had no deleterious effect on fermentative yeasts such as *Saccharomyces cerevisiae*, refuting the commonly assumed mycelytic activity of these enzymes. We note that the presence of shearing forces does not alter the compatibility in the same vessel of cellulase enzyme and fermentative yeasts. Such a reaction system can, as the saccharification alone, be operated in batch or continuous mode. In the continuous mode, a stream containing the fermentative organism, e.g. *Candida brassicae* (as well as cellulose feedstock and cellulase enzyme complex) must be continually admitted to the reactor. Pemberton and Crawford, U.S. Pat. No. 4,224,410, report that *Candida brassicae* ATCC 32196 is preferred over most fermentative microorganisms because it is capable of fermenting glucose to ethanol at up to 45° C., at which temperature the *Trichoderma reesei* cellulase enzyme is considerably more active than at 20°–30° C. Alternatively, the fermentative organism can be made to propagate in the reactor at a rate equal to its removal in the ethanol-containing effluent. This is preferable since it avoids the separate vessels required to propagate fermentative microorganisms.

The slurry withdrawn from the simultaneous saccharification and fermentation reactor contains ethanol, yeast (or other fermentative organism) cells, cellulase enzyme complex and the residue of the cellulosic feedstock which was not converted during the reaction. As discussed herein above, it is possible to operate the simultaneous saccharification and fermentation reactor disclosed herein in a "plug flow" mode; and operation in such a mode with countercurrent flow of fresh cellulosic feedstock and effluent solution, as shown schematically in Fig. 5, can be beneficial and desirable. Such a flow pattern can be maintained by pumping fresh cellulosic feed slurry into the reactor while an essentially solids-free ethanolic effluent is removed through a wiped filter port or similar device. In addition to the single reactor vessel shown in FIG. 3, multiple vessels can also be employed with various influx and efflux streams entering at the extreme terminus of the end reactors or to intermediate reactors or even at intermediate points along the vertical axis of a single reactor.

Figure 5:
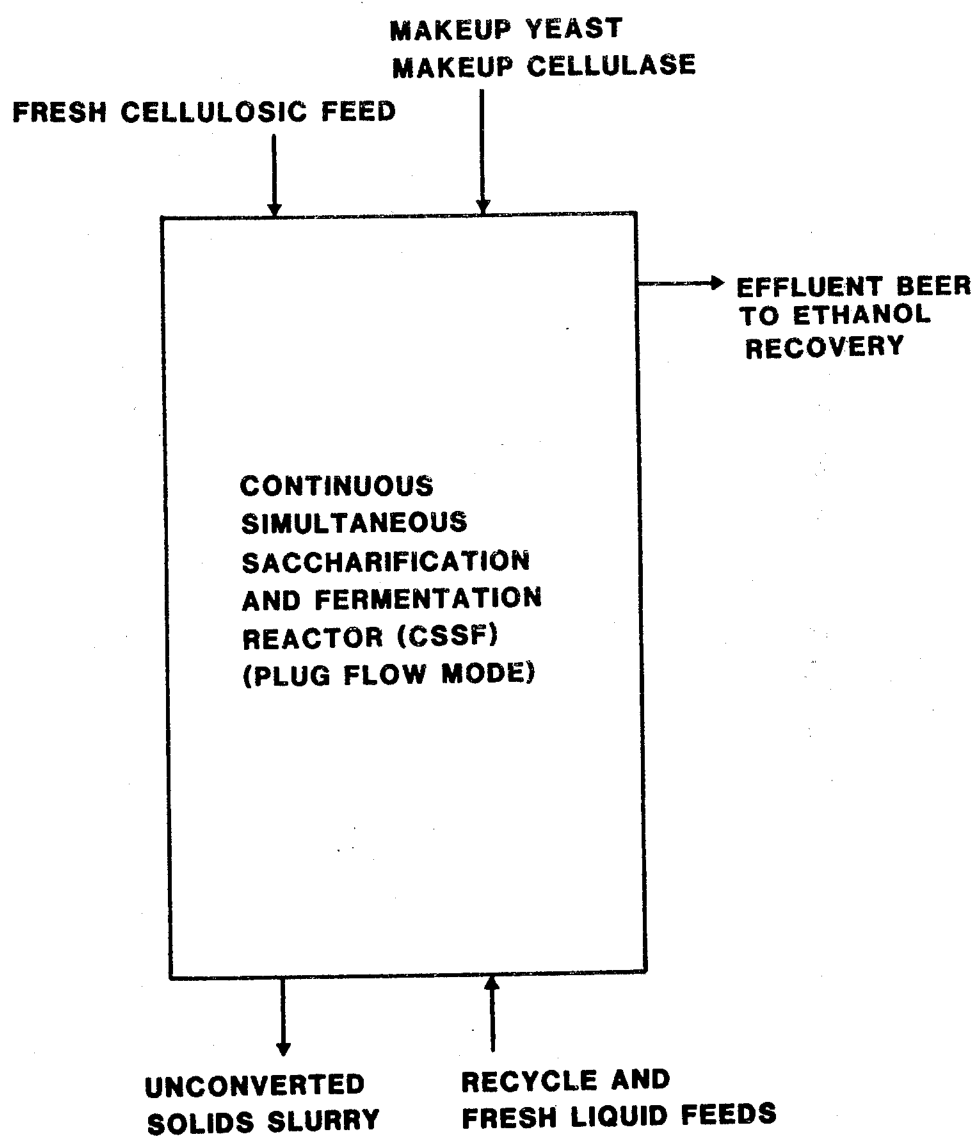
FIG. 5 shows schematically a simultaneous saccharification and fermentation operation.

It has been shown by Emert and Blotkamp, U.S. Pat. No. 4,220,721, that fresh cellulosic feedstock can adsorb part of the cellulase enzyme complex which is suspended in the effluent slurry from a simultaneous saccharification and fermentation reactor. Therefore, by operating in a plug-flow countercurrent mode as shown in FIG. 5, it is possible to recover and retain in the reactor a portion of the enzyme which would otherwise exit from the reactor.

Further recovery of enzyme, or components thereof which exit the reactor in the ethanol-containing effluent, can be achieved using the method of Emert and Blotkamp, loc. cit., in a separate vessel; and such recovered enzyme can then be recycled back to the reactor. Some make-up fresh cellulase is still required, but the cost of enzyme production is substantially reduced. In conventional practice of the enzymatic hydrolysis of cellulose to glucose, and the possible subsequent fermentation to ethanol, the cellulosic feedstock and all process vessels and input streams are thermally sterilized, e.g. by holding at about 120° C. for at least 20 minutes. This sterilization is essential because the glucose and other simple sugars formed as a result of cellulose hydrolysis accumulate in the hydrolysis vessel, and such sugars may serve as a rich nutrient for a variety of microbes which are naturally present on cellulosic materials and in the environment. Consumption of glucose by these stray microbes significantly reduces the yield of glucose from cellulose and the subsequent yield of ethanol. However, in the simultaneous saccharification and fermentation process, as disclosed by Gauss et al., whether batch or continuous, glucose never accumulates to any appreciable extent, since it is immediately consumed by the fermentative microbes which are inoculated in large numbers. Also the ethanol formed acts to inhibit various contaminating microorganisms while ethanol itself is not a nutrient for many microbes, particularly anaerobes which might grow under conditions prevalent in the reactor. Therefore, it may be permissible and economically desirable to eliminate thermal sterilization of the cellulosic feedstock and other input streams. It has been found that with most feedstocks, a mild thermal pasteurization, e.g. holding at 80° C. for one minute, is sufficient to avoid contamination of the reactor. In other cases, it has been found desirable to add low concentrations of certain antibiotics, e.g. 5 ppm streptomycin, as a further aid to avoid contamination of the simultaneous saccharification and fermentation reactor and the resulting ethanol yield loss.

Resort may be had to such variations and modifications as fall within the spirit of the invention and the scope of the appended claims.

I claim:

1. A method for the hydrolysis of cellulose to simple sugars which comprises:

contacting in a reaction zone an aqueous slurry comprising from three to 20 weight percent of a solid cellulose containing charge stock with a cellulase enzyme complex wherein the concentration of said enzyme complex is greater than 0.1 units per milliliter of said slurry and wherein said contacting occurs in the presence of a mechanically produced shear rate of from 50,000 to 200,000 feet/minute/foot substantially throughout said reaction zone and wherein the cellulose content of said solid cellulose-containing charge stock is from 30 to 80 weight percent of said charge stock.

2. A method in accordance with claim 1 wherein said shear rate is generated by a series of spaced apart rotors and stators mounted in said reaction zone containing the enzyme complex in said aqueous slurry.

3. A method in accordance with claim 2 wherein said solid cellulose-containing charge stock has a mean particle size from 0.01 to 1 inch in diameter.

4. A method in accordance with claim 2 wherein the rotors and stators comprise less than 50 percent of the reactor volume.

5. A method in accordance with claim 2 wherein the spacing between the rotors and stators is from 0.1 to 50 mm.

6. A method in accordance with claim 5 wherein said solid cellulose-containing charge stock has a mean particle size such that substantially no particles are larger than the spacing between rotor and stator blades.

7. A process in accordance with claim 1 wherein said process is operated in a conjoint presence of a fermentation microorganism for the simultaneous hydrolysis and fermentation of cellulose to ethanol.

8. A process in accordance with claim 6 wherein said fermentation microorganism is selected from the group consisting of yeasts such as *Saccharomyces cerevisiae* or *Candida brassicae* or bacteria such as *Zymomonas mobilis* or molds such as *Rhizopus javanicus.*

9. A process in accordance with claim 7 wherein the concentration of said enzyme complex is from 0.1 to 5 units per milliliter of said slurry.

10. A process in accordance with claim 8 wherein the concentration of said fermentation microorganism is such that the concentration of produced sugar is at all times substantially zero.

* * * * *

UNITED STATES PATENT OFFICE
CERTIFICATE OF CORRECTION

Patent No. 4,409,329 Dated October 11, 1983

Inventor(s) Richard S. Siver

It is certified that error appears in the above-identified patent and that said Letters Patent are hereby corrected as shown below:

Col. 8, line 5 (claim 8), "claim 6" should read --claim 7--.

Signed and Sealed this

*Thirtieth* Day of *April 1985*

[SEAL]

*Attest:*

DONALD J. QUIGG

*Attesting Officer* *Acting Commissioner of Patents and Trademarks*